United States Patent [19]
Rosengart et al.

[11] Patent Number: 5,846,225
[45] Date of Patent: Dec. 8, 1998

[54] GENE TRANSFER THERAPY DELIVERY DEVICE AND METHOD

[75] Inventors: Todd K. Rosengart, Tenafly, N.J.; Raymond A. Hartman, Carlsbad, Calif.; Charles A. Mack, III, New York, N.Y.

[73] Assignee: Cornell Research Foundation, Inc., Ithaca, N.Y.

[21] Appl. No.: 801,352

[22] Filed: Feb. 19, 1997

[51] Int. Cl.⁶ ..................................................... A61M 5/00
[52] U.S. Cl. ........................................... 604/115; 604/191
[58] Field of Search .................................... 604/131, 115, 604/134, 135, 136, 137, 191; 222/330, 548

[56] References Cited

U.S. PATENT DOCUMENTS

| | | |
|---|---|---|
| 510,413 | 12/1893 | Dolge . |
| 2,551,902 | 5/1951 | Rieck . |
| 2,670,673 | 3/1954 | Gordon et al. . |
| 3,467,096 | 9/1969 | Horn . |
| 3,572,336 | 3/1971 | Hershberg . |
| 3,595,231 | 7/1971 | Pistor . |
| 4,150,669 | 4/1979 | Latorre . |
| 4,167,179 | 9/1979 | Kirsch . |
| 5,273,525 | 12/1993 | Hofmann . |
| 5,290,258 | 3/1994 | Ennis, III et al. . |
| 5,335,670 | 8/1994 | Fishman . |
| 5,417,683 | 5/1995 | Shiao . |

*Primary Examiner*—Wynn Wood Coggins
*Assistant Examiner*—N. Kent Gring
*Attorney, Agent, or Firm*—Jones, Tullar & Cooper, P.C.

[57] ABSTRACT

A gene transfer delivery apparatus and method includes a plurality of syringes retained in a syringe-retaining portion. Each syringe contains a predetermined quantity of treatment solution. The treatment solution may be expelled through a needle on the end of each syringe by depressing the syringe plunger associated with each syringe. The syringe-retaining portion of the delivery device is connected to a plunger portion which contains a main plunger capable of depressing the syringe plungers simultaneously. Since the syringe plungers are depressed uniformly, the delivery device allows for the precise injection of a fixed volume of fluid at plural locations and at a predetermined depth. A spring-biased platen is mounted on the device for flattening the tissue prior insertion of the needles into the tissue. A method of using the delivery device for treatment of ischemic heart disease by gene therapy is also disclosed.

14 Claims, 6 Drawing Sheets

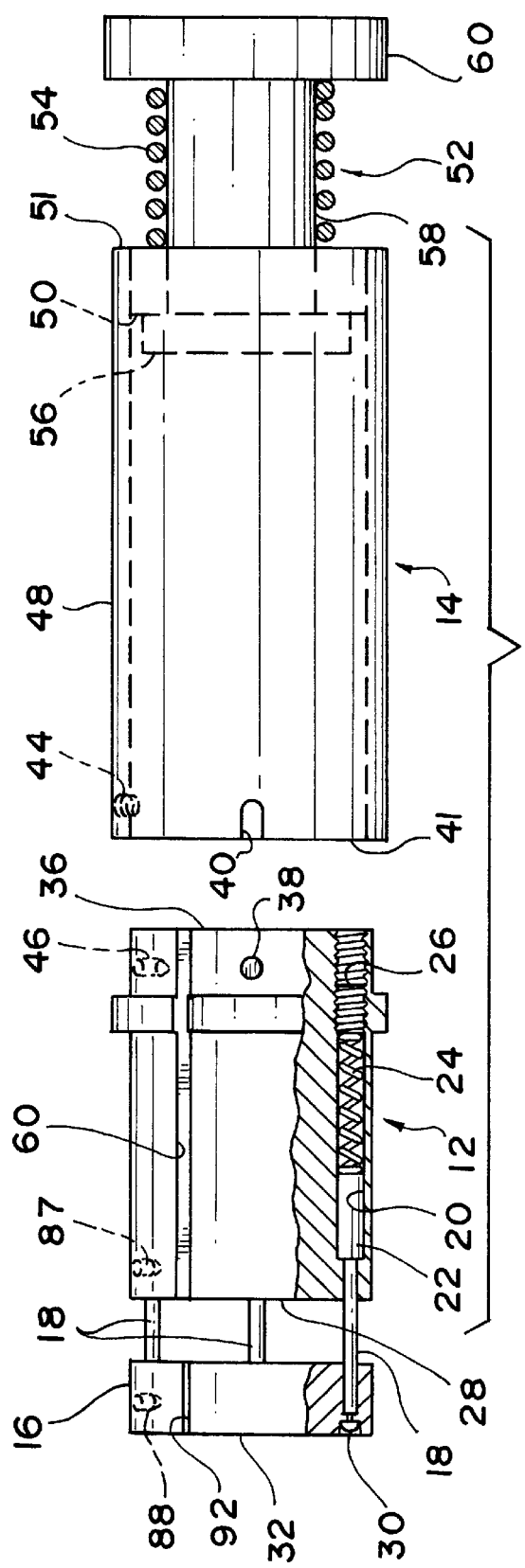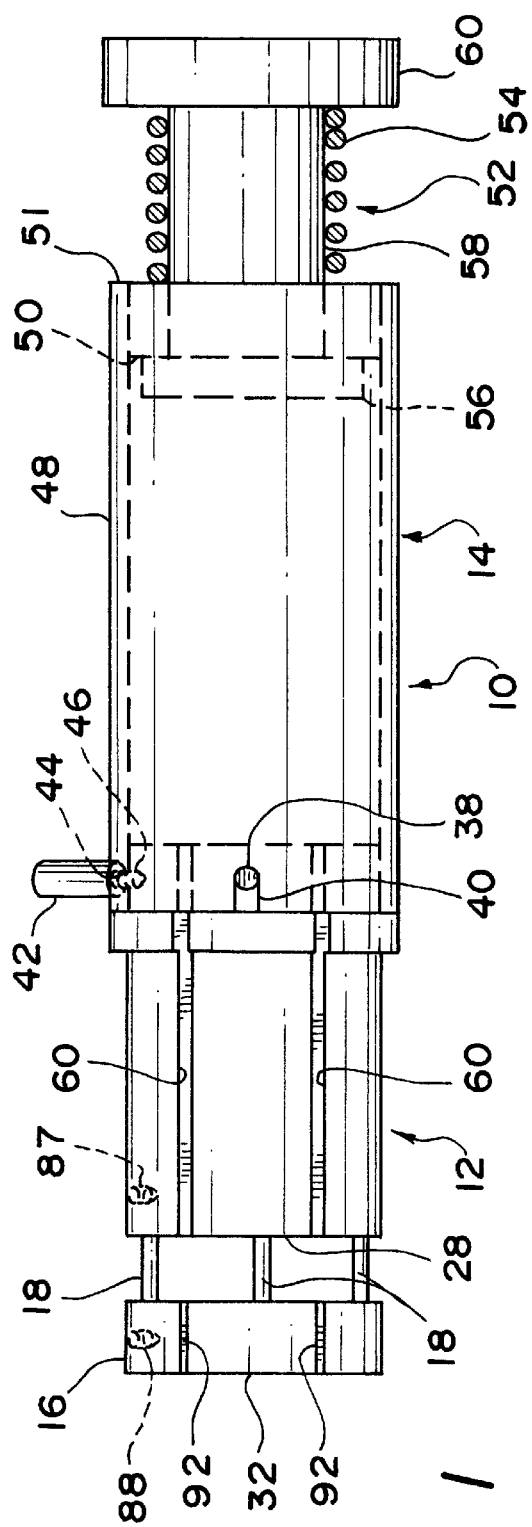

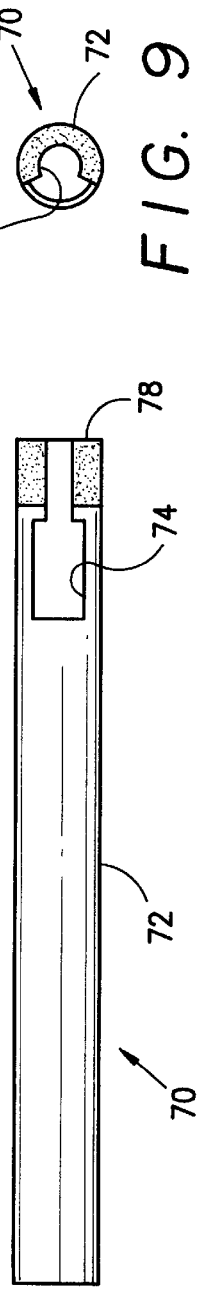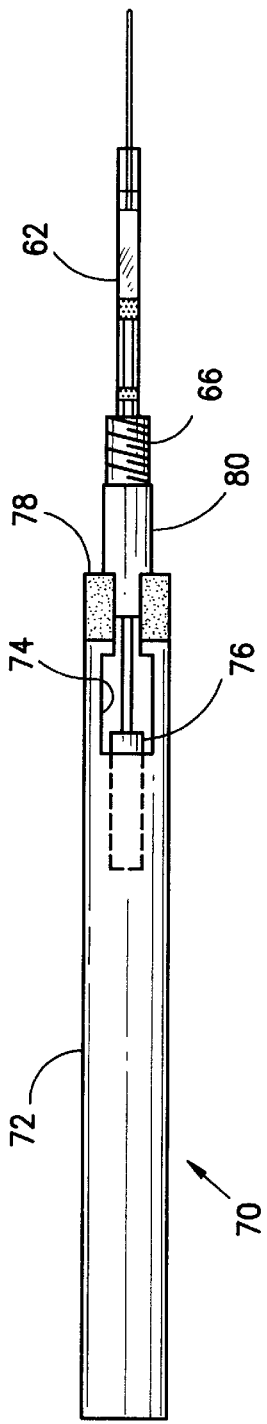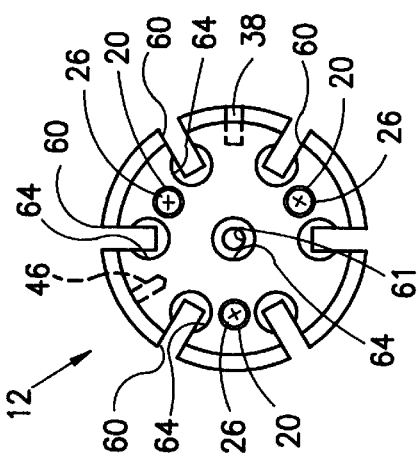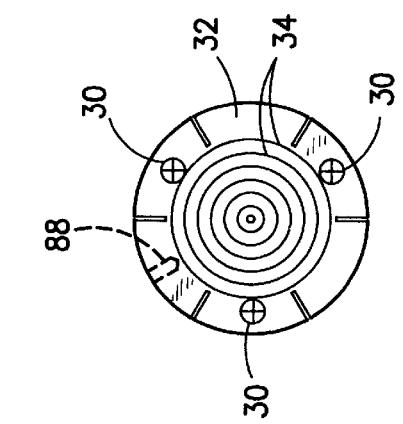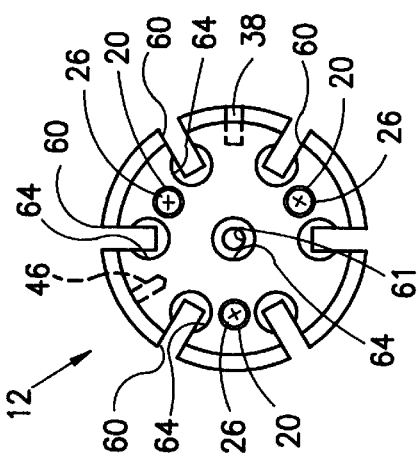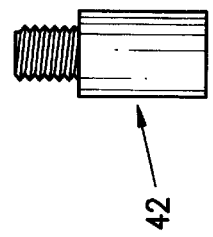

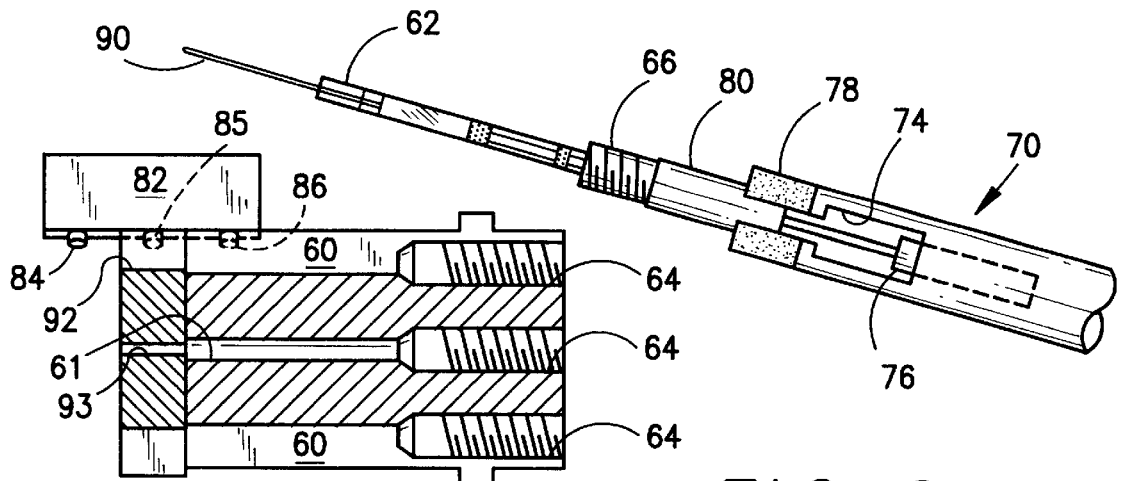
FIG. 6a
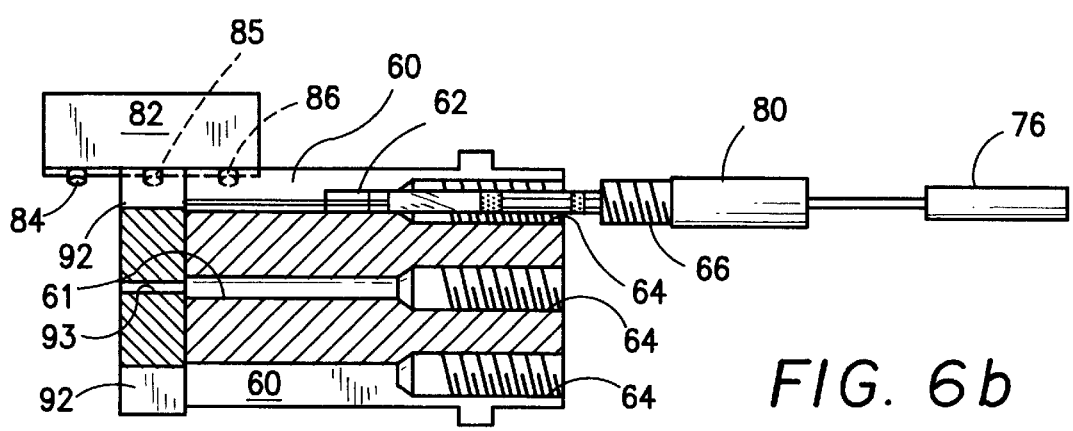
FIG. 6b
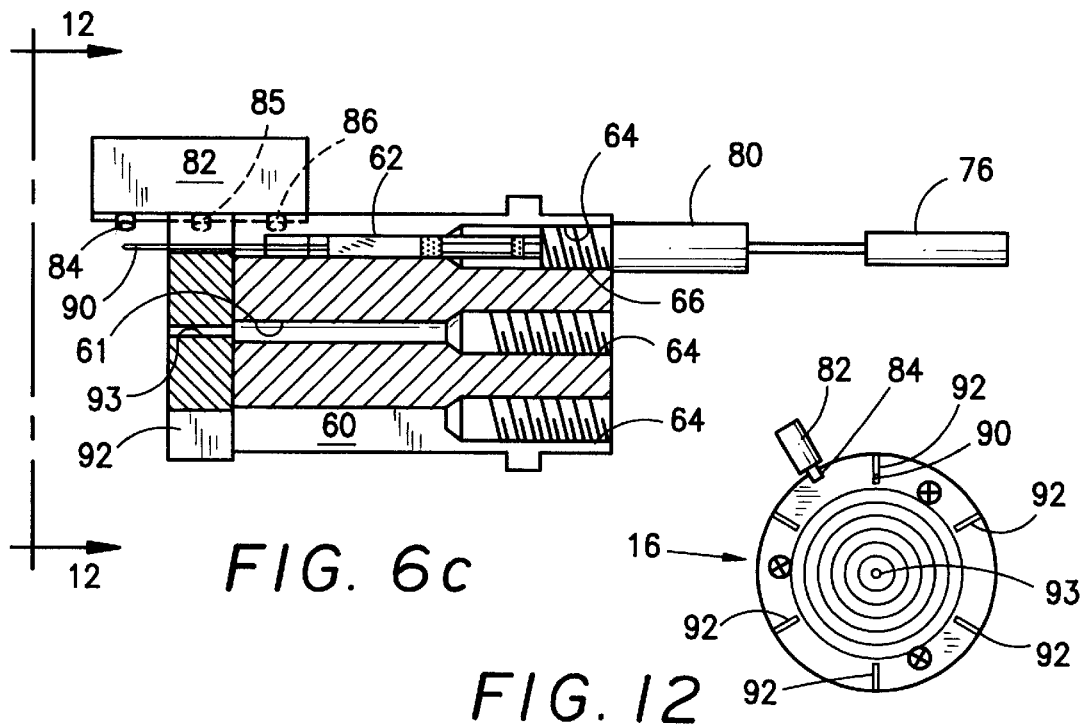
FIG. 6c
FIG. 12

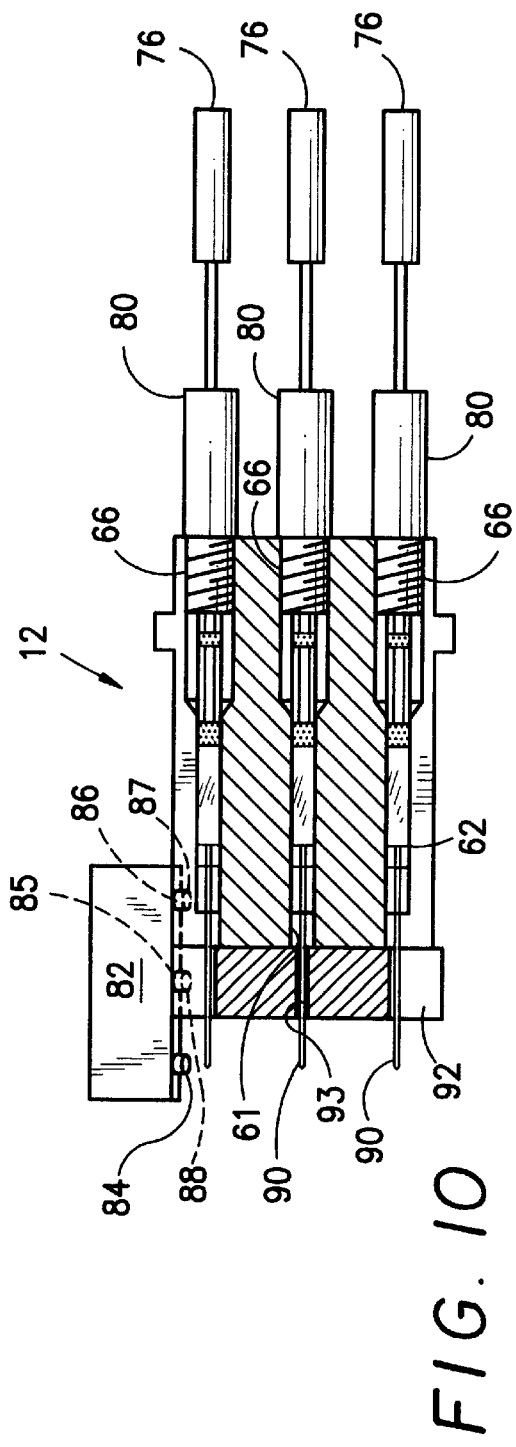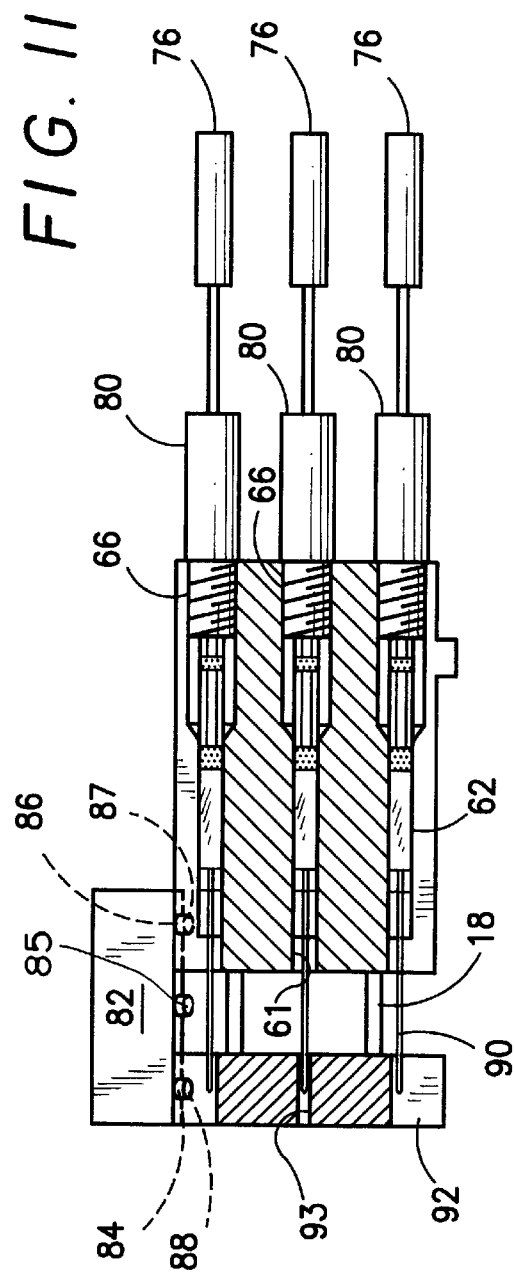

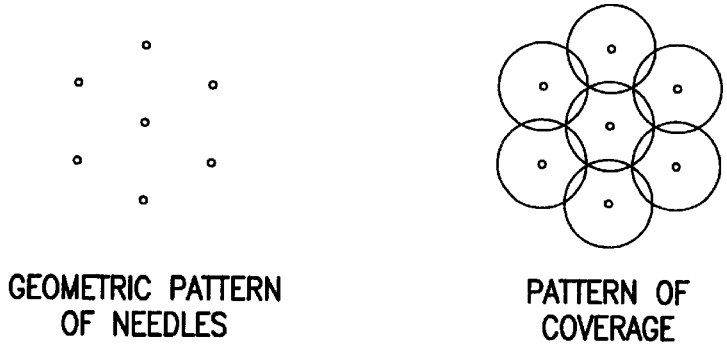
GEOMETRIC PATTERN OF NEEDLES
FIG. 15a
PATTERN OF COVERAGE
FIG. 15b
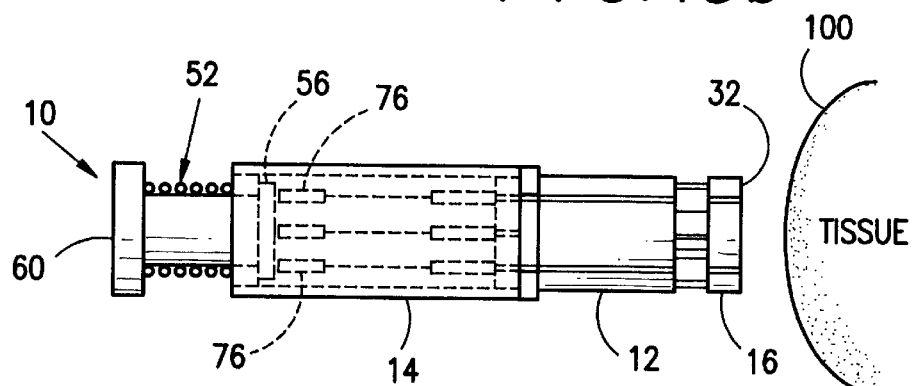
FIG. 14a
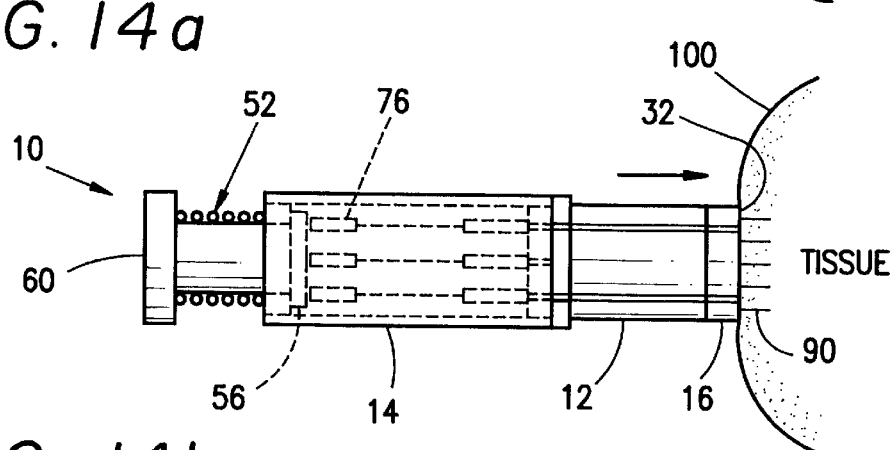
FIG. 14b
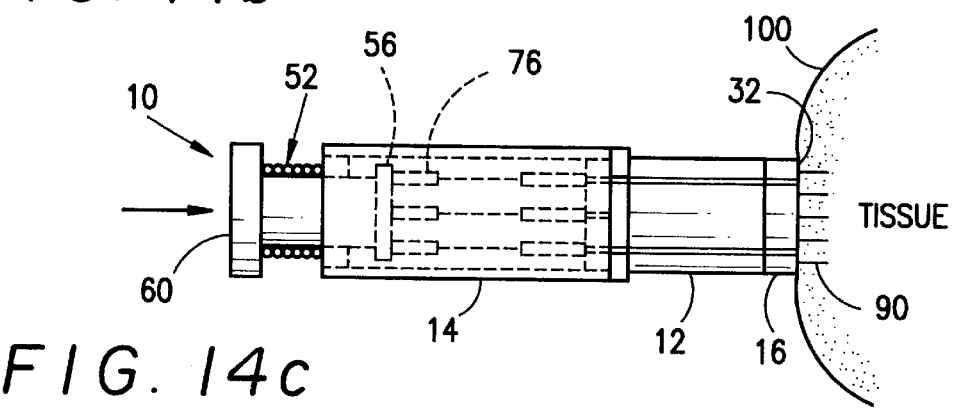
FIG. 14c

GENE TRANSFER THERAPY DELIVERY DEVICE AND METHOD

FIELD OF THE INVENTION

This invention embodies a therapeutic medical device and a method of treatment. In particular, the device is suitable for treating target tissue of a patient by injection of predetermined quantities of a substance into bodily tissue simultaneously at multiple predetermined locations. One particular application to which this invention may be applied is the delivery of therapeutic substances to the heart to induce angiogenesis and improved blood flow in heart tissue.

DESCRIPTION OF THE PRIOR ART

Despite the recent advances in the treatment of ischemic heart disease, there still exist a significant number of patients for whom conventional therapies such as angioplasty and coronary bypass surgery are not feasible options. In particular, alternative therapies are required for patients in a number of circumstances. For example, patients with diffuse small vessel coronary artery disease can not be treated by conventional coronary bypass surgery because of the small size and large number of the diseased vessel segments. In other patients re-occlusion of a diseased vessel may occur despite multiple angioplastic procedures or bypass surgeries. Thus, the need exists for alternative intervention methods.

One promising recent development in the treatment of heart disease is transmyocardial revascularization ("TMR") for providing new blood supply to ischemic heart muscle. TMR is a surgical technique aimed at providing transventricular collateral blood flow to areas of ischemic heart muscle. By the use of laser energy, channels are formed through the heart muscle into the ventricle, thereby allowing oxygen-rich intraventricular blood to flow to areas of the heart muscle that are oxygen starved due to diseased vessels.

The present clinically available laser technology employs a $CO_2$ laser as the energy source. One study using this laser on human patients showed a reduction in angina (chest pain due to oxygen-starved heart muscle) in 73% of patients one year following treatment. In another study of 12 patients who underwent the procedure, postoperative thallium stress tests and echocardiography revealed patent TMR channels with improved myocardial perfusion and function. No mortalities have been reported as occurring during or as the direct result of the TMR procedure. A phase-one preclinical trial was recently completed which demonstrated safety and channel patency after 30 days in sheep. Based upon the results of this initial TMR study, the FDA has granted an Investigational Device Exemption for the conduction of a human clinical trial which is currently underway.

Another promising treatment for ischemic heart disease is the delivery of angiogenesis-promoting substances to the heart tissue to promote angiogenesis. Angiogenesis is a complex biological process that results in the growth of new blood vessels within tissue. Angiogenesis is an essential process common to several normal and pathologic conditions including embryologic development, wound healing, development of neoplasms, and the like.

Angiogenesis has also been induced in heart tissue for reperfusion of tissue compromised by myocardial ischemia. Several growth factors have been identified and are intimately involved in initiating and promoting angiogenesis in tissue within a living body. These growth factors are typically proteins which stimulate endothelial cell reproduction in the target tissue. The tissue must be exposed to the growth factors for a period of time, i.e., a number of days. In addition, the growth factor should be limited to the target tissue so that angiogenesis is not induced in sensitive non-diseased organs, such as the retina, or in occult tumors.

The growth factor may be delivered to the target tissue through the use of indwelling catheters over a period of time. However, a preferred method of delivering the growth factor is in the form of gene transfer by a replication deficient adenoviral vector. A quantity of adenovirus having the desired genetic component is delivered to the treatment area by injection in solution. The solution containing the adenovirus is typically delivered to the tissue being treated by making a number of injections in a grid-like pattern, with the surgeon keeping track of the location of each injection. The adenovirus causes the cells in the target tissue to express the desired growth factor protein, and this protein expression from the treated cells will continue for the desired period of time. Previous studies have shown the feasibility and efficacy of safe, sustained, and localized expression of angiogenesis-promoting growth factors utilizing adenoviral mediated gene transfer therapy.

While both of the above-discussed new treatments appear promising, the subject invention sets forth a method and apparatus for improving on both of these treatments. The subject invention provides an apparatus and method for delivering angiogenesis-promoting substances to diseased tissue with greater ease and efficiency. In addition, the subject invention may be combined with TMR to further improve blood flow to areas of ischemic myocardium. These treatments could be potentially helpful to hundreds of thousands of patients with severe ischemic heart disease who are not candidates for surgical bypass or balloon angioplasty.

SUMMARY OF THE INVENTION

The present invention embodies a novel injection apparatus and method. The invention is useful, for example, in gene transfer therapy for injecting an angiogenesis-promoting factor into living tissue, such as the myocardium. The injection device includes a plurality of syringes retained in a syringe-retaining portion. Each syringe contains a predetermined quantity of treatment solution, and the treatment solution may be expelled through a needle on the end of each syringe by depressing the syringe plunger located in each syringe. The syringe-retaining portion of the delivery device is connected to a plunger portion which contains a main plunger capable of depressing all the syringe plungers simultaneously.

Since the syringe plungers are depressed uniformly, the delivery device allows for the precise injection of a fixed volume of fluid at a predetermined depth at a plurality of sites, resulting in delivery of the same volume of fluid at each injection site, regardless of pressure differentials. The injection pattern may be in the form of a grid-like arrangement, and is in accordance with the pre-arranged configuration of the syringes disposed in the injection device. Thus, various syringe configurations or injection patterns may be used in accordance with the present invention, with the syringe configuration being dependent on the desired injection pattern and volume.

Under the method of the invention, a therapeutic substance may be injected into living tissue at a plurality of locations simultaneously by a single injection. In particular, an angiogenesis-promoting factor may be introduced into myocardial territories in predetermined quantities at a plurality of points to induce the growth of bypass vessels which may allow the bridging of narrowed or occluded coronary vessels. The treatment may also be used to induce the growth of new vessels in myocardial territories poorly supplied by the native coronary vasculature.

Under an additional method of the present invention, the angiogenesis-promoting factor may be introduced into myocardial tissue following a TMR procedure. Accordingly, immediately following a TMR procedure, the ischemic areas surrounding the newly created TMR channels are injected with an angiogenesis-promoting factor in a predetermined pattern using the novel injection device. In addition, it will be apparent that the device of the subject invention is useful for other applications requiring the introduction of plural quantities of a therapeutic substance simultaneously at a plurality of locations.

BRIEF DESCRIPTION OF THE DRAWINGS

FIG. 1 is a side elevation the delivery device of the present invention prior to installation of the syringes.

FIG. 2 is a side elevation of the delivery device of FIG. 1 with the syringe-receiving portion disassembled from the plunger barrel portion.

FIG. 3 is a view taken along line 3–3.

FIG. 4 is a view taken along line 4–4.

FIG. 5 shows a thumb screw for use with the present invention.

FIGS. 6a–6c show a syringe being loaded into the syringe receiving portion of the present invention.

FIG. 7 is an elevation view of an insertion tool for use with the present invention having a syringe loaded therein.

FIG. 8 shows the insertion tool of FIG. 7 without a syringe loaded therein.

FIG. 9 is an end view of the insertion tool of FIG. 8.

FIG. 10 shows the syringe receiving portion with the platen locked in the depressed position.

FIG. 11 shows the syringe receiving portion with the platen locked in the extended position.

FIG. 12 shows a view taken along line 12–12.

FIGS. 14a–14c show the device of the present invention in use.

FIG. 15a shows a needle pattern according to the configuration of the present invention.

FIG. 15b shows the expected pattern of coverage for the injection material.

Figure 13:
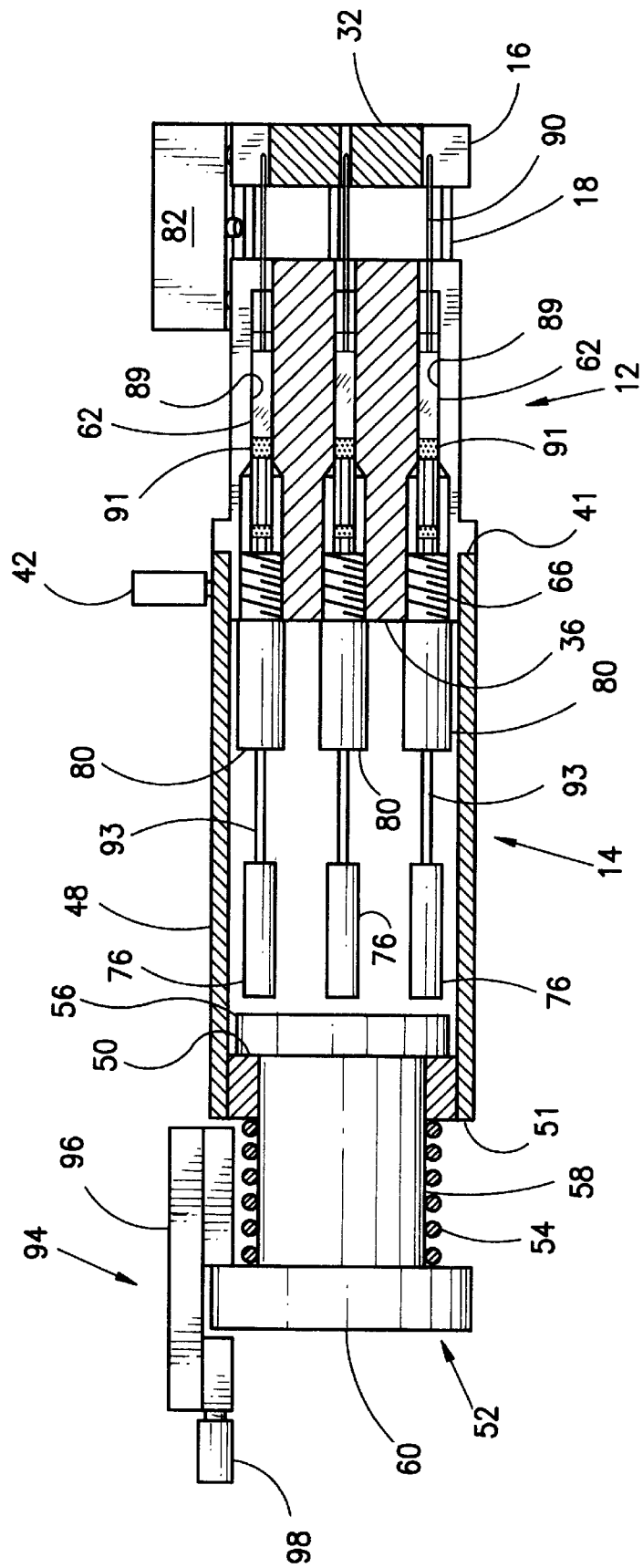
FIG. 13 shows delivery device 10 fully assembled and ready for use.

The showings of the Figures are enlarged to facilitate the disclosure of the invention.

DESCRIPTION OF THE PREFERRED EMBODIMENT

The invention is directed to a method and apparatus for delivering therapeutic treatment to body tissues. The apparatus includes a delivery device 10, as illustrated in FIG. 1, capable of receiving a plurality of pre-filled syringes for injecting a substance into bodily tissue at a plurality of injection sites simultaneously. The syringes may advantageously be arranged in a desired grid-like or other pattern so that by injecting a predetermined quantity of substance from each syringe, an entire area of tissue is treated simultaneously.

Delivery device 10 includes a syringe-receiving portion 12 and a plunger portion 14. Plunger portion 14 and syringe-receiving portion 12 are generally cylindrical in the preferred embodiment, and releasably connectable to each other, as illustrated in FIG. 2. Syringe-receiving portion 12 and plunger portion 14 may be constructed from acrylic, polyvinyl chloride, polyethylene, metal, or other suitable materials. Advantageously, the delivery device 10 may be constructed of transparent plastic, so that a surgeon may easily determine whether all the syringes are in place, and whether the syringe plungers have been depressed.

Attached to syringe-receiving portion 12 is a disc-shaped depressible platen 16. Platen 16 is pressed against the tissue to be treated during use of delivery device 10, and serves to flatten out the tissue during injection, while also serving to cover the syringe needle tips prior to and following treatment. Platen 16 is mounted on three spring-loaded rods 18, one of which is illustrated in the broken-away section of syringe-receiving portion 12 shown in FIG. 2, and as illustrated in FIGS. 3 and 4. Spring-loaded rods 18 are retained within bores 20 located radially parallel to the axis of syringe-receiving portion 12. Each rod 18 has an enlarged portion 22 which retains rod 18 within bore 20, and which contacts a spring 24. Spring 24 is retained within bore 20 by a threaded plug 26. Platen 16 is retained on rods 18 by screws 30 which are countersunk into tissue-contacting side 32 of platen 16.

Platen 16 may be depressed toward non-mating end 28 of syringe-receiving portion 12 against the spring bias created by springs 24 against each of rods 18. As platen 16 is depressed, rods 18 move further into bores 20, thereby compressing springs 24. When the pressure on platen 16 is released, the spring bias of springs 24 moves platen 16 back to its extended position. In addition, as illustrated in FIG. 3, tissue-contacting side 32 of platen 16 includes a plurality of radial ridges 34 which serve to help prevent platen 16 from slipping once it is pressed against tissue to be treated.

A mating end 36 of syringe-receiving portion 12 fits within plunger portion 14. An alignment pin 38 is located adjacent to mating end 36 and extends radially outward therefrom. Alignment pin 38 is intended to be aligned with an alignment slot 40 on plunger portion 14 when mating end 36 is inserted into the open end 41 of plunger portion 14. A thumb screw 42, as illustrated in FIG. 5 is used to retain syringe-receiving portion 12 and plunger portion 14 in an assembled state. Thumb screw 42 is inserted into a hole 44 on plunger portion 14 which aligns with a matching hole 46 on syringe-receiving portion 12 when plunger portion 14 and syringe-receiving portion 12 are properly assembled.

Plunger portion 14 includes a tubular body 48 having a shoulder 50 installed on non-open end 51. Shoulder 50 serves to retain a main plunger 52 which is spring biased in an extended position by a plunger spring 54. Plunger 52 includes a disc-shaped piston 56 located within tubular body 48. Piston 56 is mounted on a plunger rod 58 which extends through the center of plunger spring 54. A thumb pad 60 is mounted on the other end of plunger rod 58, opposite from piston 56, and is used to depress main plunger 52 by use of a thumb or other means.

As indicated above, a plurality of syringes may be loaded into syringe-receiving portion 12, substantially parallel to each other and to the longitudinal axis of syringe-receiving portion 12. Syringe-receiving portion 12 includes six radially disposed syringe slots 60 and a central syringe hole 61, with each syringe slot 60 and syringe hole 61 configured to receive a miniature syringe 62. Slots 60 and hole 61 include a threaded barrel area 64 into which may be screwed a threaded portion 66 of a syringe 62. Syringe 62 fits through slots 66 formed in syringe receiving portion 12. Syringes 62 may be inserted endwise into slots 60, or may be slid partially in sideways through slots 60 prior to being threaded into place, as illustrated in FIGS. 6a–6c. The syringe 62 to be inserted into the central hole 61 must be inserted endwise. In addition, it is preferable to insert a syringe 62 in central hole 61 first, as it is easier to do so prior to the loading of the remaining syringes 62.

Due to the small size of syringes 62 (typically 6 cm long and 2 mm in diameter) and the close spacing of slots 60 (typically 9 mm in the preferred embodiment), an insertion tool 70 is provided for making installation of syringes 62 easier. Insertion tool 70 is illustrated in FIGS. 7–9, and includes a tube 72 having an opening 74 for admission of a syringe plunger head 76. A resilient grip region 78 is located on the end of tube 72, and is constructed from silicon rubber, or the like. Grip region 78 is configured for receiving and gripping by interference fit a main body 80 of a syringe 62.

Once a syringe 62 is inserted into a slot 60 of syringe-receiving portion 12, insertion tool 70 is rotated so that syringe 62 is screwed in place. Insertion tool 70 may then be removed from syringe main body 80 by pulling it gently off and lifting away so that syringe plunger head 76 passes through opening 74 of insertion tool 70. Alternative methods of installing syringes 62 may also be used. For example, needle-nosed pliers, tweezers, or similar tools may be used in place of insertion tool 70.

For further facilitating the loading of syringes 62 into slots 60, a three-pronged key 82 is provided. Key 82 includes three prongs 84, 85, 86 for retaining platen 16 in either the depressed position (as illustrated in FIG. 10) or the extended position (as illustrated in FIG. 11). Prong 86 fits within prong hole 87 located on syringe-receiving portion 12, while either prong 84 or 85 may be inserted into prong hole 88 located on platen 16.

During loading of syringes 62 into slots 60, it is desirable to have platen 16 in the depressed position, with prong 85 located in prong hole 88. In this configuration, a needle 90 located on the end of syringe 62 may be properly aligned with a needle slot 92 or a central platen hole 93 in platen 16. As shown in FIGS. 3 and 12, needle slots 92 in platen 16 are aligned with slots 60 in syringe-receiving portion 12, and central platen hole 93 is aligned with central hole 61. When syringes 62 are fully installed in slots 60 and central hole 61, needles 90 extend into needle slots 92 and central platen hole 93. When platen 16 is in the depressed position, needles 90 extend a predetermined distance beyond tissue-contacting side 32 of platen 16. When platen 16 is in the extended position, the ends of needles 90 are protected within needle slots 92 and central platen hole 93. Following loading of syringes 62, key 82 is used to retain platen 16 in the extended position, and is removed just prior to use of delivery device 10, so that platen 16 is then freely depressible.

As is the case with conventional syringes, each syringe 62 has a tubular cylindrical lumen 89 with a movable syringe plunger 91 located within the lumen. Syringe plunger 91 is connected to plunger head 76 by a plunger rod 93, so that as plunger head 76 is depressed toward lumen 89, syringe plunger 91 moves within lumen 89 toward needle 90. A therapeutic substance may be loaded into lumen 89 and expelled through needle 90 by moving syringe plunger 91 toward needle 90. Thus, each needle 90 serves as a dispensing outlet for dispensing the therapeutic substance into bodily tissue. Syringes 62 may be constructed from plastic, metal, glass, or combinations thereof, as is known in the art.

FIG. 13 shows delivery device 10 fully assembled and ready for use. Prior to assembly, syringes 62 are filled with a predetermined amount of therapeutic substance and then loaded into slots 60 as described above. Platen 16 is then moved from the depressed position to the extended position, and locked in place using key 82 so that the tips of needles 90 are covered. Syringe-receiving portion 12 is assembled to plunger portion 14 by aligning alignment pin 38 with alignment slot 40, and inserting mating end 36 of syringe-receiving portion 12 into the open end 41 of plunger portion 14. Thumb screw 42 is installed to retain syringe-receiving portion 12 in an assembled state with plunger portion 14. A lock 94 is installed on main plunger 52 to prevent main plunger 52 from being depressed prior to the intended time. Lock 94 includes a block 96 clamped onto thumb pad 60 by a thumb screw 98.

In use, as illustrated in FIGS. 14a–14c, lock 94 and key 82 are removed from delivery device 10. Tissue-contacting side 32 of platen 16 is then pressed against tissue 100 to be treated, which may be the myocardial wall. As platen 16 is depressed against the force of springs 24, tissue 100 is flattened to conform with the flat surface of tissue-contacting side 32 of platen 16. Under continued pressure, needles 90 enter tissue 100, and platen 16 contacts syringe-receiving portion 12, as shown in FIG. 14b. The strength of springs 24 may be predetermined to ensure that tissue 100 is flattened prior to entry of needles 90 into tissue 100. This flattening action protects tissue 100 against tissue damage which may otherwise occur, prevents distortion of needles 90, and provides further benefits, as discussed in more detail below.

Next, main plunger 52 is depressed, moving piston 56 into contact with syringe plunger heads 76. As depression of main plunger 52 continues, all syringe plunger heads 76 are simultaneously depressed, thereby moving syringe plungers 91 toward needles 90, and expelling the contents of lumen 89 into tissue 100. Since there is no fluid interconnection between lumens 89 of syringes 62 (i.e., the lumens are isolated from fluid communication with each other), there is no chance that pressure differentials at the dispensing needles 90 would cause delivery of different amounts of therapeutic substance, a scenario which might occur in the case of a delivery device having a single large lumen and a plurality of delivery needles.

As illustrated in FIGS. 15a and 15b, syringes 62 are positioned within syringe portion 12 in a predetermined geometric pattern to cover a specific predetermined area of tissue. The amount of solution expelled from syringes 62 is weighed against the proximity of the needles to each other and the mobility of the solution within tissue 100. Thus, the configuration of delivery device 10 is not intended to be limited to that shown, but may include any practical number of syringes in a desired geometric pattern located a desired distance from each other. For example, delivery device 10 may have a square, rather than a circular cross section, and syringes 62 may be set up on a grid of, for example, nine syringes in a square pattern. Other alternate configurations will also be apparent to those skilled in the art, and are considered to be included within the scope of the invention.

In the preferred embodiment, however, the syringes are configured in a circular pattern, and are spaced approximately 9 mm from each other. The amount of fluid delivered will vary according to the type of treatment being administered, but is 100 $\mu$l in the embodiment shown. The spacing of the needles, the volume of therapeutic substance to be delivered, the mobility of the therapeutic substance in tissue, the desired area of coverage, and the desired depth of delivery are all factors which may be taken into account when determining the number, size, spacing, and injection pattern of the syringes.

The geometric pattern shown in FIGS. 15a and 15b provides diffuse coverage with minimal overlap, and with no uncovered areas within the overall geometry. It will be apparent that trying to provide similar coverage using a conventional single injection syringe, say, for example, in a clinical setting on a beating heart, would be subject to variation in marking, tracking, and depth of delivery, and would take considerably more time.

The distance which the needle tips extend beyond platen 16 may be adjusted from patient to patient and for particular uses by using syringes having needles of different length, by controlling how far syringes 62 are screwed into slots 60, or by controlling the thickness of platen 16. One reason for controlling the depth of needle penetration when treating ischemic heart disease is to ensure that the needle tips are located sub-epicardially, e.g., at approximately 5 mm depth.

Thus, an additional advantage of the flattening action of delivery device 10 is to ensure that all needle tips are located at the same depth within the tissue. Since the myocardial wall is normally curved outwardly, and since the exterior surface of the myocardial wall controls the needle penetration depth, inserting a plurality of spaced needles into the curved wall would result in the needles penetrating to non-uniform depths. The tissue-flattening action of the present invention thus ensures a more uniform delivery of the therapeutic substance over the entire treatment area. Alternatively, differing amounts of fluid could be delivered to different areas of tissue by controlling the quantity of fluid pre-loaded into each syringe. Furthermore, the depth of penetration of each syringe may be varied for a particular application by using syringes having needles of differing lengths or the like. In addition, it is contemplated that the syringe-receiving portion and syringes may be made of flexible material so that the device may be flexed transversely to access areas of tissue not otherwise accessible.

The device of the subject invention may be used to inject a variety of fluids into tissue for a variety of therapeutic reasons. In one preferred method of the present invention, the delivery device is used to deliver an angiogenesis-promoting compound to a portion of the myocardial wall that is suffering from insufficient blood supply. The treatment may be used independently for promoting the growth of new blood vessels, or may be used following a TMR procedure. The device of the subject invention enables quick, precise, and effective delivery of controlled quantities of the angiogenesis-promoting substance over a relatively large coverage area.

Several growth factors have been identified and are intimately involved in initiating and promoting angiogenesis. Included in this family of angiogenic growth factors are acidic fibroblast growth factor ("aFGF"), basic fibroblast growth factor ("bFGF"), and vascular endothelial growth factor ("VEGF"). VEGF in particular has been shown to be capable of promoting angiogenesis in several models of chronic ischemia, including ischemic myocardium in both porcine and canine experiments, and also in the ischemic hind limbs of lab animals.

A preferred method of delivering VEGF is in the form of cDNA or gene coding in a replication-deficient adenoviral ("Ad") vector. A quantity of adenovirus carrying the desired genetic component is delivered to the treatment area by injection in solution. Previous studies have shown the feasibility and efficacy of safe, sustained, and localized expression of VEGF utilizing adenoviral mediated gene transfer therapy.

Thus, under one method of the present invention, a predetermined quantity of angiogenesis-promoting factor is loaded into each syringe 62, and the syringes are loaded into the delivery device 10, as described above. Platen 16 is then located adjacent to the myocardial wall, by accessing the heart through open-heart surgery, through a thoracoscope, or the like. Platen 16 is then pressed against the tissue so that the tissue assumes the shape of tissue-contacting surface 32 of platen 16. Delivery device 10 is then used to deliver the angiogenesis-promoting factor to the ischemic myocardial tissue in the manner described above.

Following injection into the tissue, the angiogenesis-promoting factor initiates the complex process of angiogenesis in the treated tissue, thereby inducing the growth of new blood vessels. This treatment is of benefit to heart tissue in which the existing blood vessels are clogged or narrowed, and is also of benefit to heart tissue which is poorly supplied by the native coronary vasculature for congenital reasons.

In an additional aspect of the present invention, the present invention may combine gene transfer therapy with transmyocardial revascularization ("TMR") for providing new blood supply to ischemic heart tissue. As discussed above, TMR is a surgical technique aimed at providing transventricular collateral blood flow to areas of ischemic heart muscle. Laser energy is used to form a plurality of channels through the myocardial wall into the ventricle. This allows oxygen-rich intraventricular blood to flow to areas of the heart muscle that are oxygen starved due to diseased vessels. The present clinically available laser technology employs a $CO_2$ laser as the energy source.

Accordingly, under one method of the present invention, following a TMR treatment of ischemic heart tissue, the TMR-treated tissue is injected with an angiogenesis-promoting factor as set forth above. The device of the subject invention enables the simultaneous injection of a controlled quantity of the angiogenesis-promoting factor at a plurality of locations, giving quick and accurate coverage over the entire treatment area. In this manner, the gene therapy treatment of the present invention may be combined with a TMR treatment to obtain the benefits of both therapies.

Thus, the present invention sets forth a method and apparatus for delivering predetermined quantities of therapeutic substance to biological tissue at a plurality locations to achieve therapeutic treatment over a desired area of tissue quickly and accurately, and without requiring tracking or multiple injections. Other uses and benefits of the disclosed present invention will be apparent to those skilled in the art. Therefore, while preferred embodiments of the invention have been described herein, it will be recognized that a variety of changes and modifications may be made without departing from the spirit of the subject invention, the scope of which is set forth in the following claims.

What is claimed is:

1. A device for delivering a therapeutic substance to bodily tissue, said device comprising:

a plurality of dispensing outlets capable of penetrating the tissue for delivering a therapeutic substance to the tissue; and a platen in movably connected said dispensing outlets said platen having a surface for pressing against the tissue prior to the entry of said dispensing outlets into the tissue, whereby the tissue assumes the shape of said surface prior to penetration of said dispensing outlets into the tissue, wherein said platen is spring-biased to create a resistance so that said spring bias causes the tissue to assume the shape of said surface prior to penetration of the tissue by said dispensing outlets.

2. The device of claim 1 wherein each of said dispensing outlets is in fluid communication with a separate lumen containing a therapeutic substance for dispensing, said lumens being in fluid isolation from each other.

3. The device of claim 2 further including a main plunger for simultaneously depressing a syringe plunger disposed within each of said lumens, said syringe plungers being movable toward said dispensing outlets for expelling the therapeutic substance.

4. A device for delivering a fluid into tissue at multiple locations generally simultaneously, the device comprising:

a syringe-receiving portion adapted for receiving a plurality of pre-loaded syringes in an adjacently configured, substantially parallel manner, each syringe having a lumen for containing the fluid to be expelled into the tissue, a needle for penetrating the tissue, and a syringe plunger movable within said lumen for expelling the fluid through said needle;

a plunger portion connectable to the syringe-receiving portion and having a movable main plunger for moving said syringe plungers generally simultaneously for delivering the fluid to the tissue; and a platen movably mounted on said syringe-receiving portion for contacting the tissue prior to penetration by said needles, said platen being spring-biased to provide a resistance prior to penetration of the tissue by said needles.

5. The device of claim 4 in which said main plunger includes a piston for contacting syringe heads connected to said syringe plungers.

6. The device of claim 4 in which said syringe-receiving portion includes a plurality of slots and at least one central hole for mounting said syringes.

7. A device for delivering a fluid into tissue at multiple locations generally simultaneously, the device comprising:

a syringe-receiving portion adapted for receiving a plurality of pre-loaded syringes in an adjacently configured, substantially parallel manner, each syringe having a lumen for containing the fluid to be expelled into the tissue, a needle for penetrating the tissue, and a syringe plunger movable within said lumen for expelling the fluid through said needle;

a plunger portion connectable to the syringe-receiving portion and having a movable main plunger for moving said syringe plungers generally simultaneously for delivering the fluid to the tissue; and a platen movably mounted on said syringe-receiving portion for contacting the tissue prior to penetration by said needles, said platen being spring-biased to provide a resistance prior to penetration of the tissue by said needles, and wherein said platen covers the tips of said needles prior to contacting said platen to the tissue.

8. The device of claim 7 in which said main plunger includes a piston for contacting syringe heads connected to said syringe plungers.

9. The device of claim 7 in which said syringe-receiving portion includes a plurality of slots and at least one central hole for mounting said syringes.

10. A method of delivering multiple doses of a fluid into biological tissue generally simultaneously, the method comprising:

providing a device containing a plurality of syringes, each said syringe having a lumen for containing the fluid and a needle for dispensing the fluid, said lumens of said syringes being in fluid isolation from each other, said device including a means for generally simultaneously expelling the contents of said syringes, said device further including a platen having a surface for pressing against the tissue;

pressing said surface against the tissue so that the tissue assumes the shape of said surface;

penetrating the tissue with said needles;

expelling the contents of said syringes generally simultaneously; and wherein said platen is movably connected to the device containing the plurality of syringes and is spring biased so that the tissue assumes the shape of said surface due to spring resistance.

11. The method of claim 10 wherein said means for generally simultaneously expelling the contents of said syringes includes a syringe plunger disposed in each said syringe.

12. The method of claim 10 wherein said needles penetrate the tissue after the tissue has assumed the shape of said surface.

13. The method of claim 10 wherein said needles are arranged in a grid-like pattern.

14. The method of claim 10 wherein said needles penetrate the tissue before the tissue fully assumes the shape of said surface of said platen.

* * * * *

UNITED STATES PATENT AND TRADEMARK OFFICE
CERTIFICATE OF CORRECTION

PATENT NO : 5,846,225
DATED : December 8, 1998
INVENTOR(S) : Todd K. ROSENGART et al.

It is certified that error appears in the above-identified patent and that said Letters Patent is hereby corrected as shown below:

Col. 8, line 59
replace "in movably connected said dispensing outlets said"
with --in movable cooperation with said dispensing outlets, said--.

Signed and Sealed this

Twenty-first Day of March, 2000

Attest:

Attesting Officer

Q. TODD DICKINSON

Commissioner of Patents and Trademarks